United States Patent [19]

Cochran

[11] Patent Number: 5,047,237

[45] Date of Patent: Sep. 10, 1991

[54] ATTENUATED PSEUDORABIES VIRUS HAVING A DELETION OF AT LEAST A PORTION OF A GENE ENCODING AN ANTIGENIC, NONESSENTIAL PROTEIN, VACCINE CONTAINING SAME AND METHODS OF IDENTIFYING ANIMALS VACCINATED WITH THE VACCINE

[75] Inventor: Mark D. Cochran, Carlsbad, Calif.

[73] Assignee: PruTech Research and Development Partnership, San Jose, Calif.

[21] Appl. No.: 192,866

[22] Filed: May 11, 1988

Related U.S. Application Data

[63] Continuation of Ser. No. 887,140, Jul. 17, 1986, which is a continuation-in-part of Ser. No. 773,430, Sep. 6, 1985, Pat. No. 4,877,737, and a continuation-in-part of Ser. No. 823,102, Jan. 27, 1986.

[51] Int. Cl.$^5$ ................ A61K 39/245; G01N 33/543; C12N 15/38; C12N 15/86
[52] U.S. Cl. .................... 424/89; 436/518; 435/172.3; 435/236; 935/65; 935/81
[58] Field of Search .............. 435/68, 70, 91, 235, 435/320, 172.3; 536/27; 935/32, 34, 57, 60, 70, 72; 424/89

[56] References Cited

U.S. PATENT DOCUMENTS

| 4,356,270 | 10/1982 | Itakura | 436/317 |
| 4,514,497 | 4/1985 | Kit et al. | 436/235 |
| 4,810,634 | 7/1989 | Pont et al. | 435/235 |

Primary Examiner—Richard A. Schwartz
Assistant Examiner—S. L. Nolan
Attorney, Agent, or Firm—John P. White

[57] ABSTRACT

Attenuated pseudorabies viruses are provided which comprise DNA including a sequence essential for replication of the attenuated pseudorabies virus, at least a portion of which is present in a sequence essential for replication of a naturally-occurring pseudorabies virus. The DNA encodes mRNAs which, in an animal infected with the attenuated pseudorabies virus, are translated into antigenic pseudorabies virus gene products which invoke in the infected animal an immunological response distinguishable from an immunological response invoked in an animal infected with a naturally-occurring pseudorabies virus. Also provided are vaccines which comprise the attenuated pseudorabies virus of the present invention and methods of immunizing animals against pesudorabies virus disease.

The invention further provides a method for distinguishing an animal vaccinated with a vaccine of the present invention from an animal infected with a naturally-occuring pseudorabies virus.

7 Claims, 7 Drawing Sheets

Figure 1
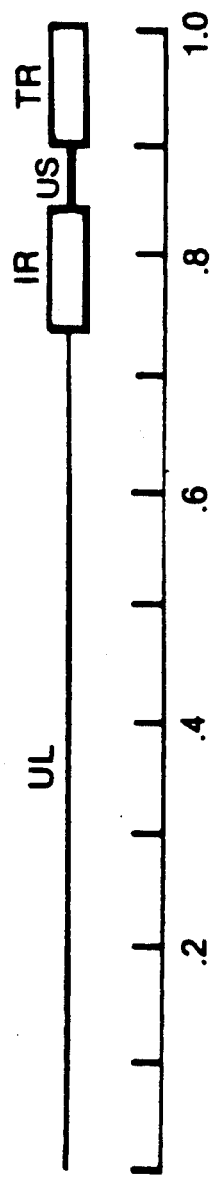
Figure 1A.
Figure 1B.

Figure 2.
Figure 2A.
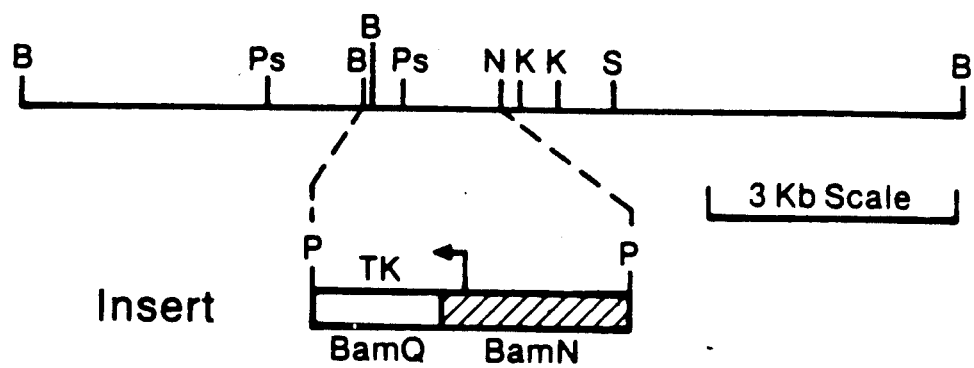
Figure 2B.
Figure 2C.
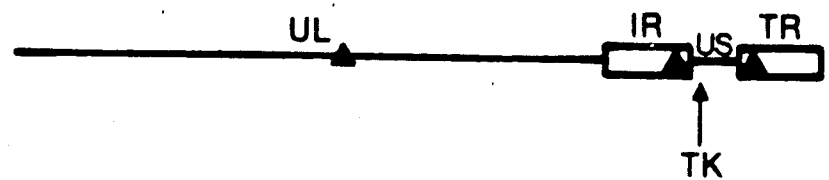

Figure 3.
Figure 3A.
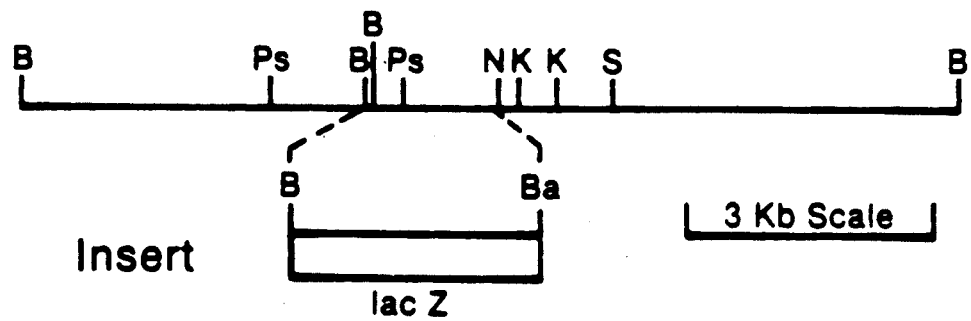
Figure 3B.
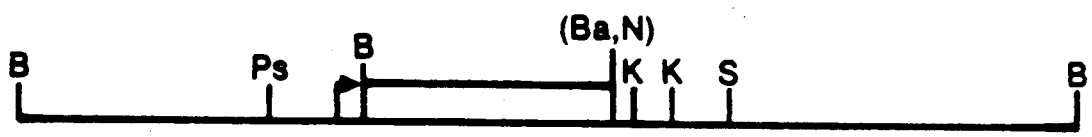
Figure 3C.
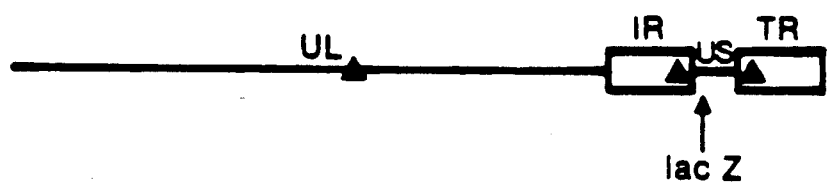
Figure 3D.
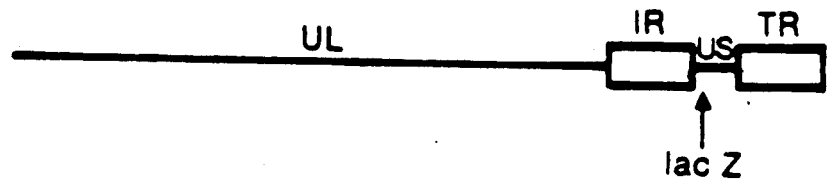
Figure 3E.
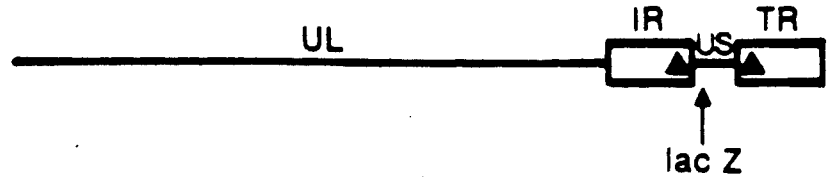

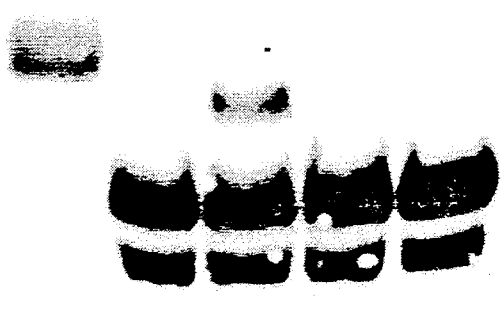

FIGURE 6
FIGURE 6A
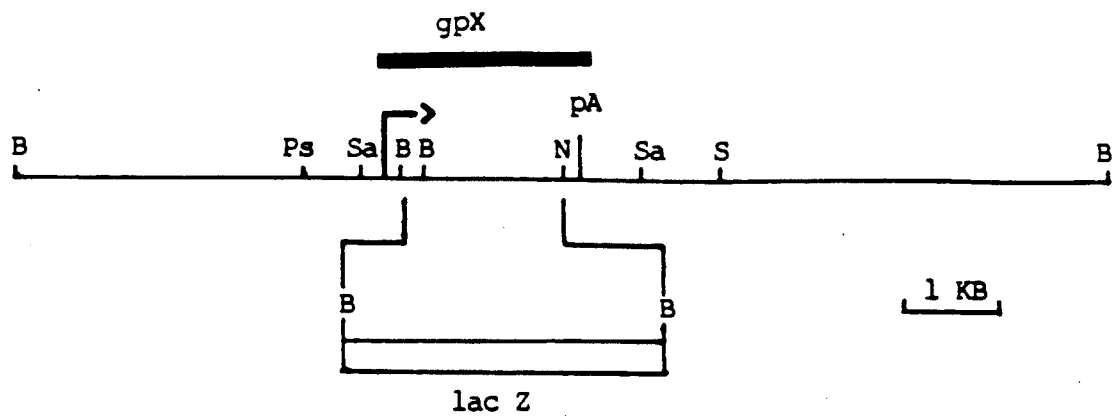
FIGURE 6B
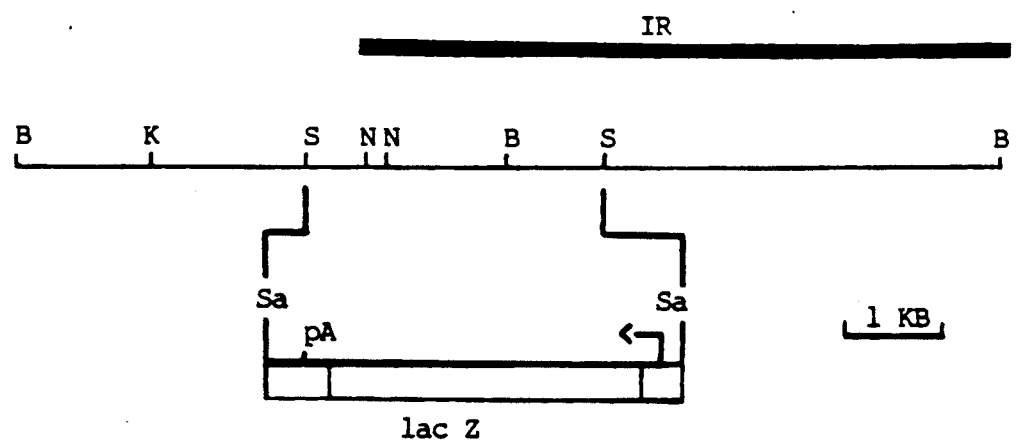
FIGURE 6C

ATTENUATED PSEUDORABIES VIRUS HAVING A DELETION OF AT LEAST A PORTION OF A GENE ENCODING AN ANTIGENIC, NONESSENTIAL PROTEIN, VACCINE CONTAINING SAME AND METHODS OF IDENTIFYING ANIMALS VACCINATED WITH THE VACCINE

This is a continuation of application Ser. No. 887,140, filed July 17, 1986, which is a continuation-in-part of U.S. Ser. No. 773,430, filed Sept. 6, 1985 now U.S. Pat. No. 4,877,737 and U.S. Ser. No. 823,102, filed Jan. 27, 1986, the contents of both of which are hereby incorporated by reference into the present application.

BACKGROUND OF THE INVENTION

Within this application several publications are referenced by arabic numerals within parentheses. Full citations for these references may be found at the end of the specification immediately preceding the claims. The disclosures of these publications in their entireties are hereby incorporated by reference into this application in order to more fully describe the state-of-the-art to which this invention pertains.

The present invention involves the ability to attenuate pseudorabies virus of swine to create a live virus vaccine and the ability to distinguish whether an animal has been given the vaccination or whether the animal has been infected by wild-type pseudorabies virus.

The ability to isolate viral DNA and to clone this DNA into bacterial plasmids has greatly expanded the approaches that can be used to make viral vaccines. The methods used to achieve the present invention involved modifying viral DNA sequences while in the cloned state in plasmids. These modifications include, but are not limited to, insertions, deletions and single or multiple base changes. The modified DNA was then inserted back into the viral genome for the purpose of rendering the virus non-pathogenic. The resulting live virus can be used in the form of a vaccine to elicit an immune response in a host animal and be protective against a disease or in any other situation wherein a non-pathogenic viral infection of an animal is required.

One group of animal viruses, the herpesviruses or herpetoviridae, is an example of a class of viruses amenable to this approach. These viruses contain 100,000 to 150,000 base pairs of DNA as their genetic material, and several areas of the genome have been identified that are dispensible for the replication of virus in vitro in cell culture. Modifications of these regions of the DNA are known to lower the pathogenicity of the virus, i.e. to attenuate the virus, for an animal species. For example, inactivation of the thymidine kinase gene renders human herpes simplex virus non-pathogenic (1), and pseudorabies virus of swine non-pathogenic (2 and 3).

Removal of part of the repeat region renders human herpes simplex virus non-pathogenic (4 and 5). A repeat region has been identified in Marek's disease virus that is associated with viral oncogenicity (6). A region in herpesvirus saimiri has similarly been correlated with oncogenicity (7). However, modifications in these repeat regions do not teach the construction of attenuated pseudorabies viruses with deletions in repeat sequences.

A region in pseudorabies virus has been shown to be deleted in naturally occurring vaccine strains (8). This deletion is partly responsible for the lack of pathogenicity of these strains, however it does not occur in a repeat sequence and does not suggest the attenuation of pseudorabies virus by deleting a portion of a repeat sequence.

It is generally concluded that herpesviruses contain non-essential regions of DNA in various parts of the genome, and that modifications of these regions can attenuate the virus, leading to a non-pathogenic strain from which a vaccine may be derived. The degree of attenuation of the virus is important in the utility of the virus as a vaccine. Deletions which cause too much attenuation of the virus will result in a vaccine that fails to elicit an adequate immune response.

The herpesviruses are known to cause a variety of latent and recurrent infections in human and other vertebrates and are even known to infect a fungus and an oyster. Among the conditions associated with herpesvirus infections are fever blisters caused by herpes simplex type 1, genital herpes causes by herpes simplex type 2, and chickenpox in children and shingles in adults cause by herpes zoster infection. Pseudorabies virus (PRV), a Class D herpesvirus, induces Aujesky's disease, an acute and often fatal nervous condition, in domestic and wild animals.

The natural host of pseudorabies virus is swine, in which infection is commonly inapparent but may be characterized by fever, convulsions and paralysis. Pseudorabies virus also infects cattle, sheep, dogs, cats, foxes and mink, where infection usually results in death of the host. The predominant visible feature of pseudorabies viral infection is intense pruritis generally resulting in host mutilation of the involved area. Violent excitement, fits and paralysis, all symptoms of encephalomyelitis, precede death which usually occurs within a few days following onset of clinical signs.

The pseudorabies virus genome has been mapped (8, 9) (see FIG. 1). The genome is known to include, in order, a unique long region, an internal inverted repeat sequence, a unique short region and a terminal inverted repeat sequence.

Pseudorabies virus disease in swine is of serious concern to governmental bodies worldwide. In the United States, swine from infected herds cannot be sold except to slaughterhouses. Several individual states have separately enacted eradication control practices against pseudorabies. At the current time, any animal vaccinated for pseudorabies disease is treated as though it were infected with pseudorabies virus and is subject to the same regulatory constraints. This is due primarily to the lack of a diagnostic test to differentiate vaccinated from infected animals.

The research and development trend among traditional vaccine manufacturers has generally emphasized research leading to vaccines that are based upon virus subunits rather than live viruses. This departure from live virus vaccines is due partly to the recognized safety aspect of subunit vaccines, and their unlikelihood of containing infectious live viruses. Another reason for developing a subunit vaccine has been to allow for the development of a diagnostic test that would accompany the vaccine and would differentiate vaccinated from infected animals, thereby escaping from the regulatory burden following use of other vaccines.

Subunit vaccines also have limitations. They contain a limited number of viral antigens compared to those produced by live viruses. This paucity of antigens produces a weak immune response of short duration in the vaccinated animal at considerably greater cost than a live virus vaccination. However, the limited spectrum of antigens in the subunit vaccine allows the vaccinated swine to be distinguished from swine which have been infected with the wild-type virus. The ability to distinguish vaccinated from infected swine is a crucial property of a pseudorabies vaccine because none of the known vaccines prevent the vaccinated animals from being super-infected by the wild-type virus. While the vaccinated animals do not become sick upon super-infection, there is strong evidence that they may become carriers of the wild-type virus and pass the wild-type virus to other swine.

In any eradiciation program aimed at eliminating pseudorabies virus, a vaccine provided with characteristics which would allow vaccinated animals to be distinguished from animals infected with wild-type virus would be advantageous. The subunit vaccines have high cost and poor efficacy but an animal vaccinated with this type of vaccine will produce antibodies only to the limited spectrum of antigens present in the vaccine. By sampling the serum of the swine, it is possible to show that the vaccinated animal has antibodies only to the antigens contained in the vaccine while an animal infected with the wild-type virus would have antibodies against a wider range of antigens. A subunit vaccine used in this way to differentiate vaccinated from pseudorabies infected animals has been disclosed in European Patent Application No. 8540074.4, filed on September 4, 1985, published November 27, 1985 as European Publication No. 0162738 and entitled "Production of Pseudorabies Virus Subunit Vaccines". This published patent application does not teach or suggest the construction or use of a similar diagnostic test in conjunction with a live virus vaccine. The vaccination of an animal with a live virus which would result in an immune response distinguishable from wild-type infection would also have the further advantages of low cost and high efficacy associated with live virus vaccines.

Deletions in genes coding for viral antigens have been described previously. A spontaneous deletion in the glycoprotein C gene of herpes simplex virus (13), a spontaneous deletion in the glycoprotein A gene of Marek's disease virus (14), a spontaneous deletion in the glycoprotein A gene (also called glycoprotein gI) of PRV (8,19) and the absence or greatly reduced amount of glycoprotein gIII in some PRV mutants (18) are known. However, all of these deletions arose spontaneously in an uncontrolled process. Hence, it has not been possible to direct deletions to DNA encoding for specific antigens to control the deletion process and direct the deletions to antigens particularly suitable as diagnostic markers.

The presence or absence of particular antigens in any infectious disease can be exploited as a diagnostic test for the infectious disease agent. This presence or absence forms the basis for all immunolgoical diagnositc tests, which differ only in the details of their specific immunological approach. Publications pertinent to the current invention include Wathan and Wathan (18) who reported that either the gI gene or the gIII gene could be deleted from PRV and suggested that the resulting virus could be used for distinguishing vaccinated from infected swine. However, they did not describe the methodology necessary to create the vaccine, they did not demonstrate the utility of such a vaccine in serological tests and they did not in any other way prove the feasibility of such a vaccine.

Van Oirschot, et al. (22), have used a special monoclonal-based immunological detection system for gI of PRV and have shown that pigs inoculated with naturally-occurring vaccine strains which are missing at least a portion of the gI gene can be differentiated from pigs infected by wild-type PRV. However, this diagnostic test may be used for any of several vaccines against PRV that are already existing in both Europe and the U.S. without differentiating which vaccine was used. This limits the usefulness of this diagnostic, since the vaccines which are detectable have differing biological and virulence properties.

The approach of deleting a gene to attenuate a virus coupled with a diagnostic for that gene, provides a vaccine that can be differentiated from any of the currently used PRV vaccines and from wild-type PRV. It is important to be able to differentiate a new, safer vaccine from those currently used because pigs receiving the current vaccines are all regulated during eradication programs to the same extent as those infected with wild-type PRV.

Antigens of choice for the purpose of a diagnostic marker would have the following characteristics: 1) the antigens and their genes would be non-essential for the production of infectious virus in tissue culture; and 2) the antigen would elicit a major serological response in the animal, but is preferably not an important neutralizing antigen.

SUMMARY OF THE INVENTION

The present invention provides an attenuated pseudorabies virus comprising DNA which includes a sequence essential for replication of the attenuated pseudorabies virus, at least a portion of which is present in a sequence essential for replication of a naturally-occurring pseudorabies virus. This DNA encodes, in an animal infected with the attenuated pseudorabies virus, mRNAs which are translated into antigenic pseudorabies virus gene products which invoke in the infected animal an immunological response distinguishable from an immunological response invoked in an animal infected with a naturally-occurring pseudorabies virus.

BRIEF DESCRIPTION OF FIGURES

FIG. 1: Details of Wild-Type Shope Strain PRV
  A. Diagram of PRV genomic DNA showing the unique long region (UL), the unique short region (US), the internal repeat region (IR) and the terminal repeat region (TR).
  B. BamHI restriction enzyme map of PRV. Fragments are numbered in order of decreasing size.

FIG. 2: Details of S-PRV-012 Construction and Map Data
  A. Detailed map of PRV extending from BamHI #10 through BamHI #7.
  B. Detailed map of PRV extending from BamHI #10 through BamHI #7 after the insertion of the TK gene into the recombinant virus.
  C. Diagram of the S-PRV-012 DNA genome showing the location of the TK gene inserted into the gpX region and the creation of a deletion that removes most of the coding region of the gpX gene and renders the virus unable to synthesize the gpX polypeptide.

Restriction Enzyme Legend: B=BamHI; K=KpnI; N=NdeI; P=PvuII; Ps=PstI; S=StuI.

FIG. 3: Details of S-PRV-013, S-PRV-014, and S-PRV-016 Construction and Map Data
  A. Detailed map of PRV extending from BamHI #10 through BamHI #7.

B. Detailed map of PRV #10 extending from BamHI through BamHI #7 after the insertion of the lac Z gene into the recombinant virus.

C. Diagram of the S-PRV-013 DNA genome showing the location of the lac Z gene inserted into the gpX region and the creation of a deletion that removed most of the coding region of the gpX gene and rendered the virus unable to synthesize the gpX polypeptide. Other deletions in the TK regions and repeat regions are shown by Δ.

D. Diagram of the S-PRV-014 DNA genome showing the location of the lac Z gene inserted into the gpX region and the creation of a deletion that removed most of the coding region of the gpX gene and rendered the virus unable to synthesize the gpX polypeptide. There are no other deletions in this virus.

E. Diagram of the S-PRV-016 DNA genome showing the location of the lac Z gene inserted into the gpX region and the creation of a deletion that removed most of the coding region of the gpX gene and rendered the virus unable to synthesize the gpX polypeptide. Other deletions in the repeat regions are shown by Δ.

Restriction Enzyme Legend: B=BamHI; Ba=BalI; K=KpnI; N=NdeI; Ps=PstI; S=StuI.

FIG. 4: Western blot of proteins released into the medium of PRV infected cells, showing the absence of gpX in S-PRV-012 and S-PRV-013 but its presence in wild-type PRV-000. Lanes: (A) molecular weight markers, (B) uninfected Vero cells, (C) wild-type PRV, (D) S-PRV-012, (E) S-PRV-013.

Figure 5:
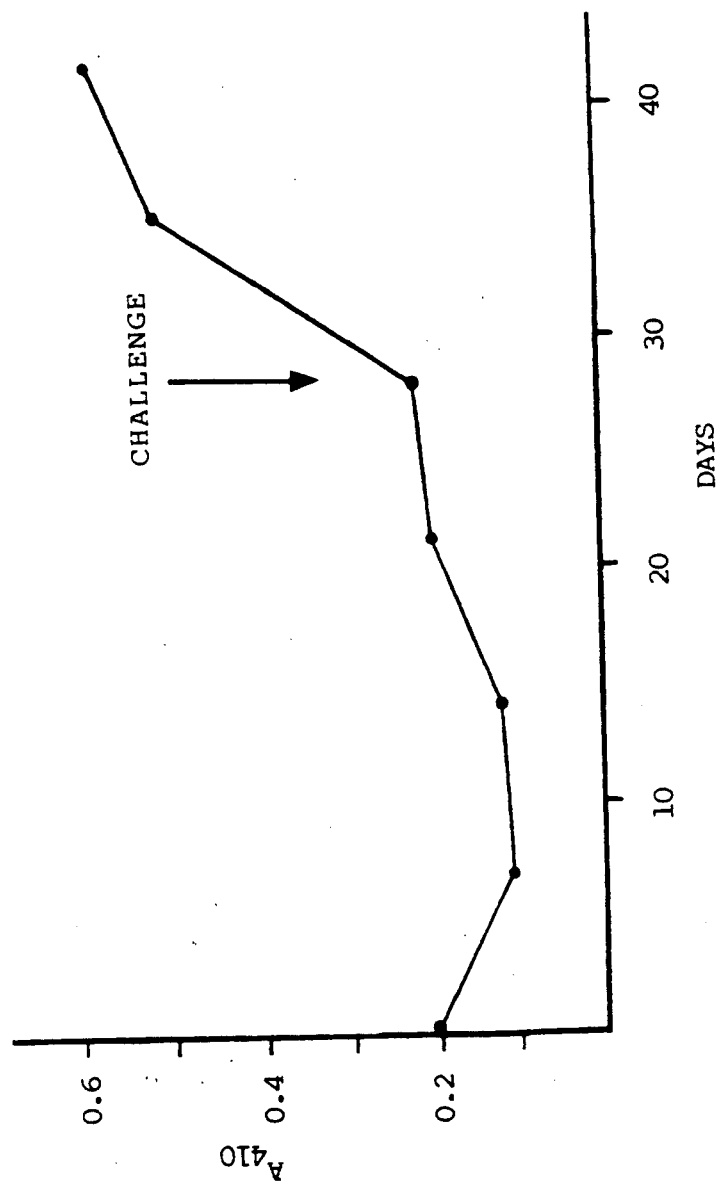

FIG. 5: Diagnostic test for the presence of antibodies against gpX in the serum of a pig vaccinated with S-PRV-013 on Day 0 and challenged with wild-type pseudo-rabies virus on Day 28.

FIG. 6: Details of S-PRV-029 Construction and Map Data

A. Detailed map of PRV extending from BamHI #10 through BamHI #7 showing the lac Z gene that will replace the gpX gene.

B. Detailed map of PRV extending from BamHI #8' through BamHI #8 at the junction of the unique long region and the internal repeat region (IR). The lac Z gene as a SalI fragment will replace the DNA between the StuI sites bracketing the junction.

C. Diagram of the S-PRV-029 genome showing the locations of the lac Z genes in the gpX region and the junction region.

Restriction Enzyme Legend: B=BamHI; Ps=PstI; Sa=SalI; N=NdeI; S=StuI; Ba=BalI; K=KpnI.

Figure 7A:
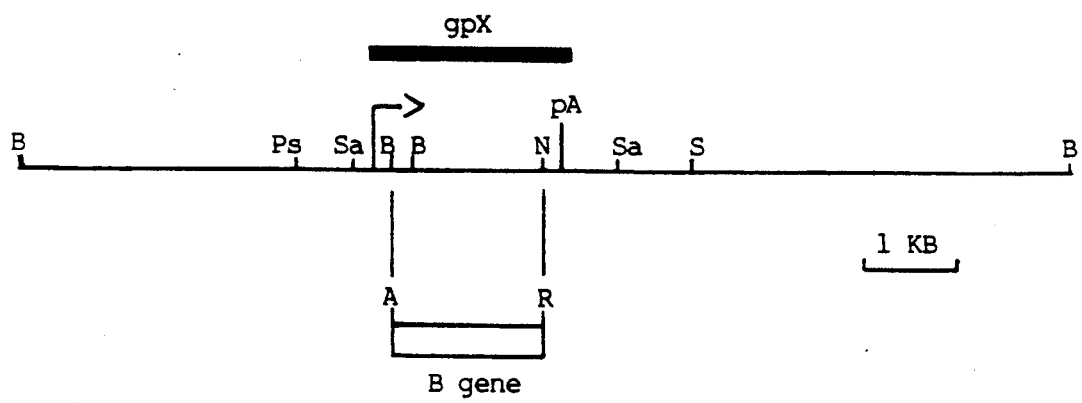
Figure 7B:
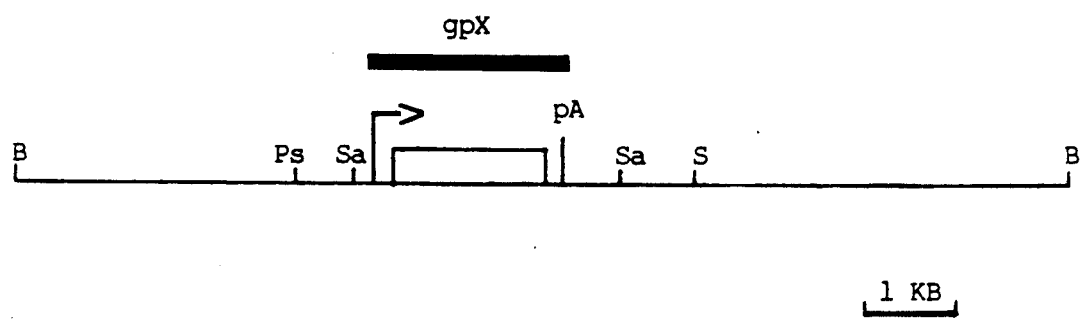
Figure 7C:
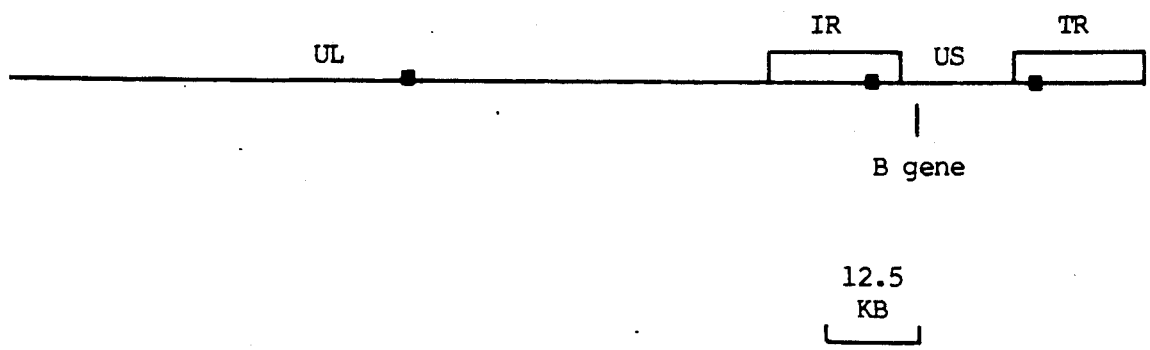

FIG. 7: Details of S-PRV-020 Construction and Map Data

A. Detailed map of PRV extending from BamHI #10 through BamHI #7 showing the parvovirus B gene that will replace the gpX gene.

B. Detailed map of PRV from BamHI #10 through BamHI #7 after the insertion of the swine parvovirus B gene in place of the gpX gene.

C. Diagram of the S-PRV-020 genome showing the location of the swine parvovirus B gene inserted into the gpX region of PRV.

Restriction Enzyme Legend: B=BamHI; Ps=PstI; Sa=SalI; N=NdeI; S=StuI; A=AccI; R=RsaI.

DETAILED DESCRIPTION OF THE INVENTION

The present invention provides an attenuated pseudorabies virus comprising DNA which includes a sequence essential for replication of the attenuated pseudorabies virus, at least a portion of which is present in a sequence essential for replication of a naturally-occurring pseudorabies virus. This DNA encodes mRNAs which, in an animal infected with the attenuated pseudorabies virus, are translated into antigenic pseudorabies virus gene products which invoke in the infected animal an immunological response distinguishable from an immunological response invoked in an animal infected with a naturally-occurring pseudorabies virus. Within this application, a naturally-occurring pseudorabies virus means a pseudorabies virus which has not been genetically engineered, and includes, but is not limited to, wild-type pseudorabies viruses and pseudorabies viruses selected from pseudorabies viruses which exist in nature and have spontaneous deletions.

The sequence essential for replication of the attenuated pseudorabies virus may be derived from a naturally-occurring pseudorabies virus. Additionally the DNA may comprise wild-type pseudorabies viral DNA from which at least a portion of a nonessential gene has been deleted. Within this application, nonessential gene means a gene which is not essential for viral replication.

In one embodiment of the invention, the nonessential gene of which at least a portion has been deleted is the gpX gene. In another embodiment of the invention, substantially all of the gpX gene coding region, a portion of a repeat sequence and the thymidine kinase gene are deleted. In yet another embodiment of the invention, substantially all of the gpX gene coding region, a portion of a repeat sequence and the thymidine kinase gene are deleted and the herpes simplex virus-1 (HSV-1) thymidine kinase gene under the control of the ICP4 promoter is inserted in place of the deleted gpX gene coding region. This virus, designated S-PRV-012, has been deposited with the American Type Culture Collection (ATCC) under Accession No. VR 2119.

In still a further embodiment of the invention, the gpX gene coding region, a portion of a repeat sequence and the thymidine kinase gene are deleted and the E. coli beta-galactosidase gene is inserted in place of the deleted gpX gene coding region. The inserted beta-galactosidase gene is under the control of the endogenous gpX promoter. This virus, designated S-PRV-013, has been deposited with the ATCC under Accession No. VR 2120.

The present invention further provides a vaccine for pseudorabies virus disease which comprises an effective immunizing amount of an attenuating pseudorabies virus of the present invention and a suitable carrier. The suitable carrier may be a physiologically balanced culture medium containing stabilizing agents. Additionally, the effective immunizing amount, i.e. an amount necessary to invoke the production of antibodies by the animal which confer protection on the animal against subsequent infection by wild-type pseudorabies virus, may be from about $10^3$ to about $10^6$ plaque forming units (PFU)/dose. Moreover, the effective immunizing amount may be from about $10^4$ to about $10^5$ PFU/dose.

In one embodiment of the invention, the vaccine comprises an effective immunizing amount of the attenuated pseudorabies designated S-PRV-012 and a suitable carrier. In yet another embodiment, the vaccine comprises an effective immunizing amount of the attenuated pseudorabies virus designated S-PRV-013 and a suitable carrier.

The present invention also provides a method of immunizing an animal against pseudorabies virus disease. This method comprises administering to the animal a suitable dose of a vaccine of the present invention. In one embodiment of the invention, the effective immunizing amount of the attenuated pseudorabies virus of the vaccine is from about $10^3$ to $10^6$ PFU/dose. Moreover, the animal may be a swine. In another embodiment of the invention, the effective immunizing amount of the attenuated pseudorabies virus of the vaccine is from about $10^4$ to about $10^5$ PFU/dose The animal immunized by this method may be a swine, dog, cat, sheep or bovine animal. In yet another embodiment of the invention, an animal may be immunized against pseudorabies virus disease by administering to the animal a suitable dose of a vaccine of the present invention which comprises the attenuated pseudorabies virus S-PRV-012. The immunized animal may be a swine. Still another method of immunizing an animal against pseudorabies virus disease comprises administering to the animal a suitable dose of the vaccine of the present invention which comprises the attenuated pseudorabies virus S-PRV-013. Furthermore, the immunized animal may be a swine.

The present invention also provides a method for distinguishing an animal vaccinated with a vaccine of the present invention from an animal infected with a naturally-occurring pseudorabies virus. This method comprises analyzing a body fluid of the animal for the presence of antigens normally expressed in an animal infected with a naturally-occurring pseudorabies virus, identifying antigens which are present in the body fluid and antigens which are not present in the body fluid and correlating said antigens which are not present in the body fluid with antigens which are not expressed in an animal infected with the attenuated pseudorabies virus of the vaccine. The presence in the body fluid of antigens which are normally expressed in the animal by a naturally-occurring pseudorabies virus except for those antigens which are not expressed in the animal by the attenuated pseudorabies virus of the vaccine would be indicative of an animal vaccinated with the vaccine and not infected with a naturally-occurring pseudorabies virus.

In one embodiment of the invention the presence of antigens in the body fluid is determined by detecting in the body fluid antibodies specific for the antigens.

Also provided is a method for distinguishing an animal vaccinated with a vaccine comprising the attenuated pseudorabies virus S-PRV-012 from an animal infected with a naturally-occurring pseudorabies virus. According to this method, a body fluid of the animal is analyzed for the presence of glycoprotein X and at least one other antigen normally expressed in the animal by a naturally-occurring pseudorabies virus. Antigens which are present in the body fluid are identified and the presence or absence of glycoprotein X in the body fluid is determined. The presence of antigens which are normally expressed in the animal by a naturally-occurring pseudorabies virus and the absence of glycoprotein X in the body fluid would be indicative of an animal vaccinated with the vaccine and not infected with a naturally-occurring pseudorabies virus. In another embodiment of the invention the presence of antigens and glycoprotein X in the body fluid is determined by detecting in the body fluid antibodies specific for the antigens and glycoprotein X.

The present invention further provides a method for distinguishing an animal vaccinated with a vaccine which comprises the attenuated pseudorabies virus S-PRV-013 from an animal infected with a naturally-occurring pseudorabies virus. This method comprises analyzing a body fluid of the animal for the presence of glycoprotein X and at least one other antigen normally expressed in an animal by a naturally-occurring pseudorabies virus. Antigens which are present in the body fluid are identified and the presence or absence of glycoprotein X in the body fluid is determined. The presence of antigens which are normally expressed in an animal by a naturally-occurring pseudorabies virus and the absence of glycoprotein X in the body fluid would be indicative of an animal vaccinated with the vaccine and not infected with a naturally-occurring pseudorabies virus. The presence of the antigens and glycoprotein X may be determined by detecting in the body fluid antibodies specific for the antigens and glycoprotein X.

Furthermore, the present invention provides a method for preparing a pseudorabies virus vaccine of the present invention. In one embodiment of the invention, the attenuated pseudorabies virus is cultured in roller bottles. In another embodiment of the invention, the attenuated pseudorabies virus is cultivated in a suspension of microcarrier beads. In yet another embodiment of the invention, the attenuated pseudorabies virus is cultivated by batch fermentation.

Methods for constructing, selecting and purifying pseudorabies viruses of the present invention, as well as assay techniques for determining the immune status of swine following vaccination and challenge with wild-type pseudorabies viruses, are detailed in the following Materials and Methods section.

Materials and Methods

PREPARATION OF PSEUDORABIES VIRUS (PRV) STOCK SAMPLES

Pseudorabies virus (PRV) stock samples were prepared by infecting Vero cells at a multiplicity of infection of 0.01 plaque forming units (PFU)/cell in Dulbecco's Modified Eagle (DME) medium containing 2mM glutamine, 100 units/ml penicllin and 100 units/ml streptomycin (these components were obtained from Irvine Scientific or equivalent supplier, and hereafter are referred to as complete DME medium) plus 1% fetal bovine serum. After cytopathic effect was complete the medium and cells were harvested and the cells were pelleted at 3000rpm for 5 minutes in a clinical centrifuge. The cells were resuspended in 1/10 the original volume of medium and an equal volume of 2 times autoclaved skim milk (9% skim milk powder in $H_2O$ wgt/vol) was added. The virus sample was frozen and thawed 2 times, aliquoted and stored frozen at $-70°$ C. The titer was usually about $10^8$ PFU/ml.

PREPARATION OF PRV DNA

For PRV DNA preparation a confluent monolayer of Vero cells in a 25 $cm^2$ flask or a 60mm petri dish was infected with 100 microliters of virus sample in 1 ml medium. Adsorption proceeded for 1-2 hours at 37° C. in a humidified incubator with 5% $CO_2$ in air. After adsorption, 4 mls of complete DME medium plus 1% fetal bovine serum were added. After overnight incubation, or when the cells were showing 100% cytopathic effect, the cells were scraped into the medium with a cell scraper (Costar brand). The cells and medium were centrifuged at 3000rpm for 5 minutes in a clinical centrifuge. The medium was decanted and the cell pellet was gently resuspended in a 0.5ml solution containing 0.01M Tris pH 7.5, lmM EDTA and 0.5% Nonidet P-40 (NP40). The sample was incubated at room temperature for 10 minutes. Ten microliters of a stock solution of RNase A (Sigma) were added (stock is 10mg/ml, boiled for 10 minutes to inactivate DNase). The sample was centrifuged for 5 minutes at 3000 rpm in a clinical centrifuge to pellet nuclei. The DNA pellet was removed with a pasteur pipette or wooden stick and discarded. The supernatant fluid was decanted into a 1.5 ml eppendorf tube containing 25 microliters of 20% sodium dodecyl sulfate (Sigma) and 25 microliters proteinase-K (10mg/ml; Boehringer Mannhiem). The sample was mixed and incubated at 37° C. for 30–60 minutes. An equal volume of water-saturated phenol was added and the sample was mixed on a vortex mixer for 1 minute. The sample was centrifuged in an Eppendorf minifuge for 5 minutes at full speed. The upper aqueous phase was removed to a new Eppendorf tube, two volumes of −20° C. absolute ethanol were added and the tube was put at −20° C. absolute ethanol were added and the nucleic acid. The sample was centrifuged in an Eppendorf centrifuge at 4° C. for 5 minutes. The supernatant was decanted and the pellet was washed one time with cold 80% ethanol. The pellet was dried in a lyophilizer and rehydrated in 17 microliters of water. For the preparation of larger amounts of DNA, the procedure was scaled up to start with an 850 cm$^2$ roller bottle of Vero cells. The DNA was stored in water or 0.01M Tris pH 7.5, lmM EDTA at 4°C.

PHENOL EXTRACTION

Phenol extraction was performed on any convenient volume of DNA sample, typically between 100 microliters to 1 ml. The DNA sample was diluted in 0.01M Tris pH 7.5, lmM EDTA and an equal volume of water saturated phenol was added. The sample was mixed briefly on a vortex mixer and placed on ice for 3 minutes. After centrifugation for 3 minutes in a microfuge, the aqueous layer was removed to a new tube and was precipiated by ethanol.

ETHANOL PRECIPITATION

DNA in a sample was concentrated by ethanol precipitation. To the DNA sample was added 1/10 volume of 3M sodium acetate, pH 7.5 and 3 volumes of cold ethanol. The DNA was precipitated for 30 minutes at −70° C. or overnight at −20° C. and then pelleted by centrifugation in the microfuge for 15 minutes at 4° C. The pellet was washed once with 200 microliters of cold 80% ethanol and pelleted again for 10 minutes at 4° C. After air drying or lyophilization, the pellets were resuspended in the appropriate buffer or water.

RESTRICTION ENZYME DIGESTION

DNA was cut by restriction enzymes using the buffer recommended by the manufacturer (IBI, BRL, New England Biolabs, etc). Whenever possible, the concentration of DNA was kept below 1 microgram/50 microliters. Incubation was at 37°C. for 1–4 hours.

AGAROSE GEL ELECTROPHORESIS OF DNA

To visualize the restriction pattern of the DNA, 5 microliters of loading buffer (5X electrophorsis buffer, 0.01% bromphenol blue dye, 50mM EDTA, and 50% glycerol) were added. The sample was loaded into a lane in a horizontal submarine electrophoresis unit containing a 0.6% agarose gel. The electrophoresis buffer was 40mM Tris, 10mM EDTA, adjusted to pH 7.8 with acetic acid, and with or without 0.5 micrograms/ml ethidium bromide. The gel was run at 40–50 volts for 18 hours, removed and stained with 0.5 micrograms/ml ethidium bromide for 30 minutes, and the DNA bands were visualized on a long wavelength UV transilluminator.

PHOSPHATASE TREATMENT OF DNA

Phosphatase treatment of DNA was performed by adding 1 microliter (25 units) of calf intestinal phosphatase (Boehringer Mannheim) directly to the restriction enzyme digestion reaction and continuing the incubation for 30 minutes at 37° C. The phosphatase was inactivated for 60 minutes at 65° C prior to phenol extraction.

POLYMERASE FILL-IN REACTION

DNA was resuspended in buffer containing 50mM Tris, pH 7.4, 50mM KCl, 5mM MgCl$_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

PHENOL EXTRACTION OF DNA FROM AGAROSE

DNA bands cut from low melting point agarose gels were diluted to less than 0.5% agarose to a final concentration of 0.3M sodium acetate. The sample was heated at 65° C. to melt the agarose and then was cooled to 37° C. for 5 minutes. An equal volume of phenol was added and the sample was phenol extracted three times (see PHENOL EXTRACTION). The DNA was then ETHANOL PRECIPITATED and the pellet resuspended at a concentration of 3–6 fmole DNA/microliter.

LIGATION

DNA was joined together by the action of the enzyme T4 DNA ligase (BRL). Ligation reactions contained 10 fmoles DNA, 20mM Tris pH 7.5, 10mM MgCl$_2$, 10mM dithiothreitol (DTT), 200 micromolar ATP and 20 units T4 DNA ligase in 10 microliters final reaction volume. The ligation was allowed to proceed for 3–16 hours at 15° C. DNA fragments to be ligated together were usually added at an equi-molar ratio. Typically two different DNA fragments were joined during ligation, but joining three or four different DNA's at once was also possible.

RESTRICTION MAPPING OF DNA

Restriction mapping of DNA was performed as detailed in Maniatis et al. (15). Once it was cloned, the DNA was digested with a number of different restriction enzymes and the DNA's were analyzed on agarose gels and the sizes of the resulting fragments measured. A double digest with two different restriction enzymes was performed on the same DNA sample to aid in the interpretation of the maps. Another approach used was to cut the DNA with a restriction enzyme that has a single unique site in the DNA, label the end of the DNA with $^{32}$P using T4 DNA kinase or Klenow DNA polymerase (see POLYMERASE FILL-IN REACTION) and then cut the DNA with other restriction enzymes at low temperature or for short times so that only partial fragments on agarose gels served to order the restriction sites on the map. All of these mapping procedures are well understood by those skilled in the art and are detailed in Maniatis et al. (15). The most complete restriction maps can only be composed once the DNA has been sequenced, and the sequence is then analyzed by a computer searching for all the known restriction enzyme sites. Some of our maps have been generated from sequence information, as indicated in their textual description.

SOUTHERN BLOTTING OF DNA

The general procedure for Southern blotting was taken from Maniatis et al. (15). DNA was blotted to nitrocellulose filters (S&S BA85) in 20X SSC (1X SSC=0.15M NaCl, 0.015M sodium citrate, pH 7.0), and prehybridized in hybridization solution consisting of 30% formamide, 1X Denhardt's solution (0.02% polyvinylpyrrolidone (PVP), 0.02% bovine serum albumin, 0.02% ficoll), 6X SSC, 50mM $NaH_2PO_4$, pH 6.8, and 200 micrograms/ml salmon sperm DNA for 4-24 hours at 55° C. Labeled probe DNA was added that had been labeled by nick translation using a kit from Bethesda Research Laboratories (BRL) and one $^{32}P$-labeled nucleotide. The probe DNA was separated from the unincorporated nucleotides by a NACS column (BRL) or on a sephadex G50 column (Pharmacia). After overnight hybridization at 55° C., the filter was washed once with 2X SSC at room temperature followed by two washes with 0.1X SSC, 0.1% sodium dodecyl sulfate (SDS) for 30 minutes at 55° C. The filter was dried and autoradiographed.

DNA TRANSFECTION FOR GENERATING RECOMBINANT VIRUS

The method is based upon the calcium phosphate DNA precipitation procedure of Graham and Van der Eb (12) with the following modifications. For transfection into animal cells, 0.1-0.2 micrograms of plasmid DNA containing the foreign DNA flanked by appropriate PRV cloned sequences (the homovector) were mixed with 0.3 micrograms of intact PRV DNA. The final volume of the mixture should be less than 0.25 ml. To the mixture was added an equal volume of 2X HEPES buffered saline (10g N-2-hydroxyethyl piperazine N'-2-ethanesulfonic acid (HEPES), 16g NaCl, 0.74g KCl, 0.25g $Na_2HPO_4.2H_2O$, 2 g dextrose per liter $H_2O$ and buffered with NaOH to pH 7.4). The mixture was then diluted to 0.5 ml by the addition of the appropriate volume of 1X HEPES buffered saline (prepared by diluting the above described solution 1:1 with $H_2O$). After mixing, 35 microliters of 2.2M $CaCl_2$ were added to the DNA mixture and mixed.

The mixture was incubated at room temperature for 30 minutes. Medium was removed from an 80% confluent monolayer of rabbit skin cells or Vero cells growing in a 25 $cm^2$ flask, and the DNA mixture was added to the flask and distributed over the cells. After a 30 minute incubation at room temperature, 5 mls of complete DME medium plus 10% fetal bovine serum were added. The cells were incubated for 5 hours at 37° C. in a humidified incubator containing 5% $CO_2$ in air. The medium was changed at 5 hours either with or without a glycerol shock. When used, the glycerol shock consisted of removing the medium and adding DME containing 20% glycerol for 3 minutes at room temperature, followed by a wash with 10% glcyerol in DME, and a wash in 5% glycerol in DME, followed by the addition of fresh complete DME medium plus 10% fetal bovine serum. The cells were incubated at 37° C. as above for 3-4 days until cytopathic effect from the virus was 50-100%. Virus was harvested as described above for the preparation of virus stocks. This stock was referred to as a transfection stock and was subsequently screened for recombinant virus either with or without a selection mechanism to enrich for recombinant plaques as described below.

BROMODEOXYURIDINE SELECTION OF RECOMBINANT PRV

In order to insert a foreign gene in place of a thymidine kinase (TK) gene already present in the PRV genome, the foreign gene was cloned in plasmids so that it contained the same flanking homoglogy regions as the TK genes. These flanking regions could be parts of the TK gene itself or parts of PRV that flank the TK gene. In either case, the plasmid DNA containing the foreign gene was transfected with intact PRV genomic DNA containing the herpes simplex virus-1 (HSV-1) TK gene.

The transfection stock of recombinant virus was grown for two selections in 143 TK-cells in the presence of 40 micrograms/ml bromodeoxyuridine (BUDR, Sigma) in complete DME medium plus 10% fetal bovine serum. The drug BUDR is an analogue of thymidine that is recognized by the viral enzyme thymidine kinase and is ultimately incorporated into DNA. When incorporated into the DNA, BUDR is mutagenic and lethal and thus selects against viruses that have an active TK gene. By this selection method, viruses that had exchanged their TK gene for a foreign gene by homologous recombination were enriched in the population. Screening for the recombinant viruses was then performed by one of the techniques detailed below.

HAT SELECTION OF RECOMBINANT PRV EXPRESSING THYMIDINE KINASE

Deletion mutants of PRV which suffered deletions in the thymidine kinase (TK) gene were constructed. These PRV strains have been designated S-PRV-002 and S-PRV-003 and have been deposited with the ATCC under Accession Nos. VR 2107 and VR 2108 respectively. These TK minus (TK-) viruses have been used as recipients for the insertion of the foreign herpes simplex type 1 (HSV-1) TK gene. One HSV-1 TK gene that has been used contains the HSV-1 ICP4 promoter and was from B. Roizman (16). It was subcloned to lie between two flanking regions of PRV DNA, for example by insertion of the TK gene into PRV BamHI #5 fragment between XbaI and HpaI sites. The plasmid construct was then transfected with the PRV TK-DNA to yield recombinant virus. The transfection stock was enriched for TK-containing virus by the HAT selection procedure described in (17). The transfection stock was used to infect monolayers of 143 TK-cells in 60 mm culture dishes that had been preincubated in HAT medium for 16 hours at 37° C. (HAT medium: medium 199 containing 2 mM glutamine, 100 units/ml penicillin, 100 units/ml sterptomycin, 10% fetal bovine serum, $5 \times 10^{-5}$ M hypoxanthine, $10^{-5}$ M thymidine, $5 \times 10^{31\ 6}$ M aminopterin). Samples of the transfection stock virus were infected into the 143 TK- cells using $10^{-3}$ to $10^{-7}$ dilutions of virus. After one or two days at 37° C., the dishes inoculated with the highest dilution of virus and still showing virus plaques were harvested for virus stocks, and the selection was repeated a second time. The virus stock harvested from the second HAT selection was used in a plaque assay and individual plaques were picked and tested for foreign DNA inserts as described below.

BLUOGAL SCREEN FOR RECOMBINANT PRV

When the foreign gene encoded the enzyme beta-galactosidase the plaques that contained the gene were visualized more easily. The chemical Bluogal ™ (Bethesda Research Labs) was incorporated (200-300 micrograms/ml) into the agarose overlay during the plaque assay, and plaques that expressed active beta-glactosidase turned blue. The blue plaques were then picked and purified by further blue plaque isolations. Other foreign genes were inserted by homologous recombination such that they replaced the beta-galactosidase gene; in these instances non-blue plaques were picked for purification of the recombinant virus.

ANTIBODY SCREEN FOR RECOMBINANT PRV

A third method for screening the recombinant virus stock was to look directly for the expression of the foreign gene with antibodies. PRV plaques were spotted and picked by inserting a toothpick through the agarose above the plaque and scraping the plaque area on the dish.

Viruses were then rinsed from the toothpick by inserting the toothpick into a well of a 96-well microtiter dish (Falcon Plastics) containing a confluent monolayer of Vero cells. The Vero cells, after reaching confluency, had been washed 3 times in the complete DME medium without serum prior to picking the virus plaques. It was important for the virus to grow without serum at this stage to allow for the immunological procedure to work. After cytopathic effect was complete, the plates were put at $-70°$ C. to freeze and lyse the cells. The medium was thawed and the freeze/thaw procedure was repeated a second time. Then 50–100 microliters of medium were removed from each well and filtered under vacuum through a nitrocellulose membrane (S&S BA85) using a DotBlot ™ apparatus (BRL). The filter blots were soaked in a blocking solution of 0.01M Tris, pH 7.5, 0.1 M NaCl, 3% bovine serum albumin at room temperature for 2 hours with shaking. The filter blots were then placed in a sealable bag (Sears Seal-A-Meal ® or equivalent), and 10 mls of blocking solution were added that contained 10 microliters of antibody specific for the foreign protein. After overnight incubation at room temperature with shaking, the blot was washed 3 times with 100 ml 0.01M Tris, pH 7.5, 0.1 M NaCl, 0.05% Tween 20 detergent (Sigma) The blot was put in another sealable bag and 10 mls blocking solution were added containing $10^6$ counts per minute of $^{125}$I-protein A (New England Nuclear). After allowing the protein A to bind to the antibody for 2 hours at room temperature with shaking, the blot was washed as above, dried, and overlayed with an X-ray film and an intensifying screen (Dupont) and autoradiographed for 1–3 days at $-70°$ C. The film was developed by standard procedures. Virus from the positive wells which contained the recombinant virus was further purified.

PURIFICATION OF gpX gpX was purified from the tissue culture medium of infected Vero cells grown in complete DME plus 1% fetal bovine serum. Confluent Vero cells were infected at a multiplcity of infection equal to 5, with wild-type, Shope strain pseudorabies virus. The viral proteins were radiolabelled with $^{14}$C glucosamine and/or $^{35}$S methionine by adding the appropriate label to the flask eight hours after infection. The cells and media were harvested at twenty hours post infection, when the cells showed considerable cytopathic effect and the fluids were centrifuged.

The supernatant fluid was concentrated 10X and dialyzed against 0.02M sodium sulfate/0.01M sodium phosphate buffer, pH 7.2 (16 hours, 0° C.), then against two changes of 0.01M sodium phosphate buffer, pH 7.2 (24 hours, 0° C.). The dialysate was treated for 30 minutes at 0° C. with 70% perchloric acid to a final concentration of 0.2M perchloric acid, then centrifuged at 10,000 rpm for 25 minutes. The supernatant fluid was then dialyzed against 0.02M Tris, pH 8.5.

Purification was carried out by high performance liquid chromatography on a Beckman Model 334 HPLC.

The acid-soluble proteins were separated on a Biogel TSK DEAE 5-PW column (75×75mm) using a 60 minute linear gradient, flow rate 0.8 ml/minute. Starting buffer was 0.02M Tris, pH 8.5, limit buffer was 0.02M Tris, pH 7.0 containing 0.75M NaCl.

The gpX eluted as a major radioactive peak at 64% of the limit buffer. The recovered material represented 25% of the applied radioactivity.

ELISA ASSAY

A standard enzyme-linked immunosorbent assay (ELISA) protocol was used to determine the immune status of swine following vaccination and challenge.

A purified gpX antigen solution (40 microliters) was allowed to absorb to the wells of polycarbonate microtiter dishes for 2 hours at room temperature. The antigen was in a (0.015M) carbonate-(0.04M) bicarbonate buffer, pH 9.6. The coated wells were rinsed 3 times with ELISA wash solution (0.05% Tween 20 non-ionic detergent in phosphate buffered saline, pH 7.5).

Forty microliters of serum containing gpX antibody (diluted 1 to 10 in Tris buffer containing 1% bovine serum albumin and 0.05% Tween 20) were added to the wells and incubated 1 hour at 37° C.

The anti-serum was removed and the wells were washed 3 times with ELISA wash solution. A solution containing Staphylococcal protein A coupled to horseradish peroxidase (Bio-Rad) (diluted 1:10,000 in the Tris/BSA/Tween buffer described above) was added (50 microliters) to visualize the wells containing antibody against the specific antigen. The solution was incubated 1 hour at 37° C., then removed and the wells were washed 3 times with ELISA wash solution. 100 microliters of substrate solution (equal volumes of hydrogen peroxide and AIBS buffer (Bio-Rad)) were added to each well and color was allowed to develop for 20 minutes.

The reaction was terminated by addition of 50 microliters of 0.1 M oxalic acid. The color was read at absorbance (A) 410nm on an automatic plate reader.

VACCINATION STUDIES IN SWINE

Weaned pigs (4–6 weeks old) and pregnant sows were obtained from swine herds to be free of pseudorabies disease. Susceptibility of the test animals to pseudorabies was further verified by testing the pig serum for absence of neutralizing antibodies to pseudorabies virus (PRV). The weaned pigs and 3-to-4 day old piglets were inoculated intramuscularly with 1 ml of virus fluid containing about $10^4$ to $10^6$ infectious units (TCID$_{50}$). Animals were observed each day after vaccination for adverse reactions (clinical signs of PRV disease) and body temperatures were recorded. Samples of tonsillar secretions were obtained and cultured to determine if the vaccine virus was capable of shedding and spreading to other animals. Immunity was determined by measuring PRV serum antibody levels at weekly intervals and in some cases, by challenging the vaccinated pigs with virulent virus. In the latter case, the vaccinated animals and a group of non-vaccinated animals were inoculated with virulent, Shope strain PRV, using an amount of virus that caused PRV disease in at least 80% of the unvaccinated group of pigs. This was done about 28 days after vaccination. The challenged animals were observed daily for signs of disease and for increased body temperatures. A necropsy was conducted on animals that died and selected tissues were examined and cultured for PRV.

EXAMPLES

EXAMPLE 1

S-PRV-012

S-PRV-012 is a pseudorabies virus that has a deletion in the TK gene located in the long unique region, a deletion in the repeat region and a deletion in the short unique region encoding glycoprotein X (called gpX and identified and mapped by Rea et al.) (10). The HSV-1 TK gene under the control of the ICP4 promoter was inserted in place of the gpX gene.

The following procedure was used to make the deletion of gpX and the simultaneous insertion of the HSV-1 TK gene. The flanking regions for homology to PRV were from Cloned fragments of BamHI #10 fragment and BamHI #7 fragment extending from NdeI to BamHI (FIG. 2). The BamHI and NdeI sites were filled in according to the POLYMERASE FILL-IN REACTION, and the PvuII fragment of HSV-1 DNA was inserted by LIGATION. This plasmid was transfected with intact viral DNA from a PRV strain which has a deletion in both repeat sequences and a deletion in the thymidine kinase gene, i.e. S-PRV-002, deposited with the ATCC under Accession No. VR 2107, according to the DNA TRANSFECTION FOR GENERATING RECOMBINANT PRV procedure. The recombinant virus was selected by HAT SELECTION OF RECOMBINANT PRV procedure, and screened by the ANTIBODY SCREEN FOR RECOMBINANT PRV procedure using antibodies specific for the HSV-1 protein.

The recombinant virus selected by this procedure was designated S-PRV-012 and has been deposited with the ATCC under Accession No. VR 2119 and was shown by RESTRICTION MAPPING OF DNA and SOUTHERN BLOTTING OF DNA to contain the HSV-1 TK gene inserted in place of the PRV gpX gene (FIG. 2B). The ANTIBODY SCREEN FOR RECOMBINANT PRV procedure indicated that the virus was expressing the inserted HSV-1 TK gene. The structure of this virus is shown in FIG. 2C.

EXAMPLE 2

S-PRV-013

S-PRV-013 is a pseduorabies virus that has a deletion in the TK gene in the long unique region, a deletion in the repeat region and a deletion in the gpX coding region. The gene for *E. coli* beta-galactosidase (lacZ gene) was inserted in place of the gpX gene and is under the control of the endogenous gpX gene promoter.

The following procedures were used to construct S-PRV-013 by homologous recombination. The flanking PRV homology regions were from the cloned BamHI #10 fragment which contained the gpX promoter, and from the cloned BamHI #7 fragment extending from the NdeI site to the BamHI site (FIG. 3A). The NdeI site was filled in according to the POLYMERASE FILL-IN REACTION, and the beta-galactosidase gene was inserted between the BamHI #10 and BamHI #7 fragments. This construct positioned the beta-galactosidase gene behind the gpX promoter and the gpX poly A signal sequences with a deletion of almost all of the coding regions of gpX. The plasmid DNA and DNA from S-PRV-002, a PRV strain with a deletion in both repeat sequences and a deletion in the thymidine kinase gene, were mixed and transfected according to the DNA TRANSFECTION FOR GENERATING RECOMBINANT PRV procedure. The recombinant virus was screened and purified from the transfection stock by the BLUOGAL SCREEN FOR RECOMBINANT PRV procedure.

The resulting virus from this screen was designated S-PRV-013 and has been deposited with the ATCC under Accession NO. VR 2120. It contained the beta-galactosidase gene in place of the gpX coding regions (FIGS. 3B and 3C) as determined by PREPARATION OF PRV DNA followed by SOUTHERN BLOTTING OF DNA. The expression of the beta-galactosidase gene was confirmed by the BLUOGAL SCREEN FOR RECOMBINANT PRV test, and by the o-nitrophenylgalactopyranoside substrate assay (11).

To confirm that the coding region for gpX had been removed from S-PRV-013, DNA extracted from a stock of purified S-PRV-013 was digested with BamHI and the fragments were separated on agarose gel electrophoresis and analyzed by SOUTHERN BLOT HYBRIDIZATION. The hybridization probe was the BamHI-NDE fragment of pseudorabies BamHI #7 fragment from the unique short region. This probe fragment included 90% of the coding sequences of gpX. In this analysis, the gpX region was shown to be missing from S-PRV-013.

To confirm these results, cells were infected with either wild-type pseudorabies, S-PRV-012 or S-PRV-013, and samples of media from the infected cultures were subjected to SDS-polyacrylamide gel electrophoresis. The gel was blotted and analyzed using the WESTERN BLOT PROTOCOL. The anti-serum used was a rabbit hyperimmune serum raised against a chemically-synthesized gpX antigenic peptide linked to bovine serum albumin. As shown in FIG. 4, gpX is prominent in the media of cells infected with wild-type virus (PRV 000), but is not detected in the media of cells infected with S-PRV-012 or S-PRV-013. These results demonstrate that the gpX gene is missing from both S-PRV-012 and S-PRV-013 and the protein, gpX, is not produced in cells infected by either S-PRV-012 or S-PRV-013.

The following experiments indicate that S-PRV-013 may be used as a vaccine to protect swine against psuedorabies disease and that it produces an immune response which can readily be distinguished from wild-type infection.

In the first study, susceptible weaned pigs and four-day old piglets were vaccinated intramuscularly with S-PRV-013 as follows: 4 of each group were inoculated with $10^6$ $TCID_{50}$ and 4 were inoculated with $10^4$ $TCID_{50}$ of virus. The animals were observed, then challenged as described in VACCINATION STUDIES WITH SWINE (see Table I below).

TABLE I

RESPONSES OF 4-DAY-OLD PIGLETS VACCINATED WITH S-PRV-013 AND CHALLENGED WITH VIRULENT PRV

| Pig Group | Vaccine Dose | Pig No. | Post-Vaccination Antibody Day 14 | Day 21 | Day 28 | Clinical Signs[a] | Virus Isolation | Post-Challenge Antibody Day 7 | Day 14 | Clinical Signs |
|---|---|---|---|---|---|---|---|---|---|---|
| WEANED | $10^6$ TCID$_{50}$ | 1 | 4 | 3 | 2 | NEG | NT[b] | >64 | >64 | NEG |
|  |  | 2 | 4 | 2 | 2 | NEG | NT | >64 | >64 | NEG |
|  |  | 3 | 2 | 2 | 2 | NEG | NT | 64 | >64 | NEG |
|  |  | 4 | 4 | 2 | 4 | NEG | NT | >64 | >64 | NEG |
|  | $10^4$ TCID$_{50}$ | 5 | 2 | 2 | 2 | NEG | NT | >64 | >64 | NEG |
|  |  | 6 | <2 | <2 | 2 | NEG | NT | 64 | >64 | NEG |
|  |  | 7 | <2 | <2 | <2 | NEG | NT | 64 | >64 | NEG |
|  |  | 8 | <2 | <2 | <2 | NEG | NT | 64 | >64 | NEG |
| PIGLETS | $10^6$ TCID$_{50}$ | 10 | 8 | 16 | 32 | NEG | NEG | >64 | >64 | NEG |
|  |  | 11 | —[c] | — | — | NEG | NEG | — | — | — |
|  |  | 12 | 8 | NT | 64 | NEG | NEG | >64 | >64 | NEG |
|  |  | 13 | 4 | 8 | 32 | NEG | NEG | >64 | >64 | NEG |
|  | $10^4$ TCID$_{50}$ | 14 | 4 | 8 | 32 | NEG | NEG | >64 | >64 | NEG |
|  |  | 15 | 8 | 16 | 32 | NEG | NEG | >64 | >64 | S |
|  |  | 16 | 2 | 2 | 8 | NEG | NEG | 64 | >64 | NEG |
|  |  | 17 | 4 | 16 | 32 | NEG | NEG | 64 | 64 | NEG |
|  | Contact Control | 18 | <2 | <2 | <2 | NEG | NEG | 2 | 16 | F, C |
|  |  | 19 | —[d] | — | — | NEG | NEG | — | — | — |
| Challenge Control |  | 20 | Not Applicable | | | | | <2 | — | F, C, D |
|  |  | 21 |  | | | | | <2 | 2 | F, C |
|  |  | 22 |  | | | | | <2 | 2 | F, C |

[a] Key to clinical signs: NEG = Negative, C = CNS, D = Death, F = Febrile, R = Respiratory, S = Scours
[b] Not tested
[c] Sacrificed Day 4 post-vaccination
[d] Sacrificed Day 7 post-vaccination; runt doing poorly Following vaccination, all animals were free of adverse reactions and all but 2 (weaned pigs) developed serum neutralizing antibody titers of 1:2 to 1:64. Virus was not recovered from tonsillar swabs of any pig or from tissues taken from the piglet (#11) sacrificed on Day 4. One of 2 contact control piglets (#19) was sacrificed 7 days into the experiment because it was a runt and doing poorly. Tissues from this piglet were negative when cultured for PRV. The other contact control remained healthy and did not develop PRV antibody prior to challenge.

After challenge, all vaccinated animals remained clinically normal and developed secondary antibody responses. The contact control piglet and the three challenge control pigs all developed typical central nervous system signs of PRV and one control died following challenge.

In a second study with S-PRV-013 using larger numbers of animals, 2 litters of susceptible 3-day-old piglets and a group of 15 susceptible weaned pigs were vaccinated with $10^4$ TCID$_{50}$ of virus, then challenged as described in VACCINATION STUDIES WITH SWINE (see Tables II and III below).

TABLE II

RESPONSES OF 3-DAY-OLD PIGLETS VACCINATED WITH S-PRV-013 AND CHALLENGED WITH VIRULENT PRV

| Group | Pig No. | Post-Vaccination Antibody Day 7 | Day 14 | Day 21 | Day 28 | Clinical Signs[a] | Virus Isolation | Post-Challenge Antibody Day 7 | Day 14 | Clinical Signs | Virus Isolation |
|---|---|---|---|---|---|---|---|---|---|---|---|
| LITTER A VACCINATES | 1 | <2 | 2 | 4 | 4 | F[b] | Neg | 32 | >64 | Neg | Neg |
|  | 2 | <2 | 8 | 8 | 16 | F | Neg | 64 | >64 | Neg | Neg |
|  | 3 | <2 | 8 | 8 | 16 | F | Neg | 16 | 32 | Neg | Neg |
|  | 4 | <2 | 8 | 16 | 16 | F | Neg | 32 | >64 | Neg | Neg |
|  | 6 | <2 | 8 | 8 | 16 | F | Neg | 64 | >64 | Neg | Neg |
| Contact Control | 7 | <2 | <2 | <2 | <2 | Neg | Neg | 2 | 2 | C, F, R | Neg |
|  | 8 | <2 | <2 | <2 | <2 | Neg | Neg | <2 | >64 | C, F | Neg |
| LITTER B VACCINATES | 10 | <2 | 8 | 8 | 16 | F | Neg | 16 | >64 | Neg | Neg |
|  | 11 | <2 | 8 | 8 | 16 | F | Neg | 32 | >64 | Neg | Neg |
|  | 12 | <2 | 8 | 32 | 32 | F | Neg | 32 | >64 | Neg | Neg |
|  | 13 | <2 | 4 | 16 | 32 | F | Neg | 64 | >64 | Neg | Neg |
|  | 14 | <2 | 8 | 16 | 32 | Neg | Neg | 64 | >64 | Neg | Neg |
|  | 16 | <2 | 4 | 4 | 16 | F | Neg | 32 | >64 | Neg | Neg |
|  | 17 | <2 | 8 | 8 | 32 | F | Neg | 64 | >64 | Neg | Neg |
| Contact Control | 18 | <2 | <2 | <2 | <2 | Neg | Neg | 2 | 2 | C, F | Neg |
| CHALLENGE CONTROLS | 19 | Not Applicable | | <2 | | Not Applicable | | 2 | 2 | C, F, R | Neg |
|  | 20 |  | | <2 | | | | <2 | 2 | C, F, R | Swab |
|  | 21 |  | | <2 | | | | 2 | <2 | C, F, R | Swab |
|  | 22 |  | | <2 | | | | <2 | 2 | C, F, R | Swab |
|  | 23 |  | | <2 | | | | <2 | Died | C, D, F, R | Swab Tonsil, CNS |

TABLE II-continued

RESPONSES OF 3-DAY-OLD PIGLETS VACCINATED WITH
S-PRV-013 AND CHALLENGED WITH VIRULENT PRV

| Group | Pig No. | Post-Vaccination | | | | | | Post-Challenge | | | |
|---|---|---|---|---|---|---|---|---|---|---|---|
| | | Antibody | | | | Clinical Signs[a] | Virus Isolation | Antibody | | Clinical Signs | Virus Isolation |
| | | Day 7 | Day 14 | Day 21 | Day 28 | | | Day 7 | Day 14 | | |
| | 24 | | | <2 | | | | <2 | 2 | C, F, R | Swab |

[a]Clinical signs: NEG = Negative, C = CNS, D = Death, F = Febrile, R = Respiratory
[b]1° F. increase in temperature was obseved in day 1 in these vaccinates

TABLE III

RESPONSE OF WEANED PIGS VACCINATED WITH
S-PRV-013 AND CHALLENGED WITH VIRULENT PRV

| Group | Pig No. | Post-Vaccination | | | | | Post-Challenge | | | |
|---|---|---|---|---|---|---|---|---|---|---|
| | | Antibody | | | Clinical Signs[a] | Virus Isolation | Antibody | | Clinical Signs | Virus Isolation |
| | | Day 0 | Day 14 | Day 21 | | | Day 7 | Day 14 | | |
| VACCINATES | 35 | <2 | <2 | 4 | Neg | Neg | >64 | >64 | Neg | Neg |
| | 36 | <2 | 2 | 2 | Neg | Neg | >64 | >64 | Neg | Neg |
| | 37 | <2 | 2 | 2 | Neg | Neg | >64 | >64 | Neg | Neg |
| | 38 | <2 | <2 | 2 | Neg | Neg | >64 | >64 | Neg | Neg |
| | 39 | <2 | 2 | 2 | Neg | Neg | 64 | 64 | Neg | Neg |
| | 40 | <2 | 2 | 4 | Neg | Neg | >64 | >64 | Neg | Neg |
| | 41 | <2 | 2 | 4 | Neg | Neg | 64 | >64 | Neg | Neg |
| | 42 | <2 | 2 | 4 | Neg | Neg | >64 | >64 | F | Neg |
| | 43 | <2 | 2 | 2 | Neg | Neg | >64 | >64 | F | Neg |
| | 44 | <2 | 2 | 2 | Neg | Neg | 64 | >64 | F | Neg |
| | 45 | <2 | 2 | 4 | Neg | Neg | >64 | >64 | Neg | Neg |
| | 46 | <2 | 2 | 2 | Neg | Neg | >64 | >64 | Neg | Neg |
| | 47 | <2 | <2 | 2 | Neg | Neg | 32 | >64 | F | Neg |
| | 48 | <2 | 2 | 2 | Neg | Neg | >64 | >64 | F | Neg |
| | 49 | <2 | 2 | 2 | Neg | Neg | 64 | >64 | F | Neg |
| CONTROLS | 30 | <2 | NT[b] | <2 | Not Applicable | | <2 | 4 | C, F, R | Neg |
| | 31 | <2 | NT | <2 | | | <2 | 2 | C, F | Neg |
| | 32 | <2 | NT | <2 | | | 2 | 4 | C, F, R | Neg |
| | 33 | <2 | NT | <2 | | | <2 | Died | C, D, F, R | Tonsil, CNS |
| | 34 | <2 | NT | <2 | | | <2 | 4 | F | Neg |

[a]Clinical signs: NEG = Negative, C = CNS, D = Death, F = Febrile, R = Respiratory
[b]Not tested In this experiment, all of the vaccinated animals remained healthy following vaccination, developed serum neutralizing antibody to PRV and did not shed vaccine virus in tonsillar secretions. After challenge with virulent virus, vaccinates of both age groups remained free of PRV disease, whereas the 3 non-vaccinated contact controls and 10 of 11 of the challenge controls developed severe pseudorabies disease.

The serum samples collected from the vaccinated and challenged swine were assayed by the gpX ELISA assay. Because the gene for gpX was deleted from S-PRV-013, it is expected that swine vaccinated with S-PRV-013 would be sero-negative in the ELISA test for this antigen. The challenge virus carries the gpX gene. The vaccinated animals were protected by the vaccination from pseudorabies disease when challenged with the wild-type virus. However, vaccinated animals were asymptomatically super-infected by the challege strain and would, therefore, be expected to produce antibodies to gpX upon challenge.

As shown in FIG. 5, serum from an animal vaccinated with S-PRV-013 remained negative for gpX until after challenge with the wild-type virus. These results indicate that S-PRV-013 is an effective vaccine strain which permits vaccinates to be distinguished from animals infected with wild-type virus by a simple serum diagnostic assay.

EXAMPLE 3

S-PRV-014

S-PRV-014 is a pseudorabies virus that has a deletion in the gpX coding region. The gene for *E. coli* beta-galactosidase was inserted in place of the gpX gene and is under the control of the endogenous gpX gene promoter.

The following procedures were used to construct S-PRV-014 by homologous recombination. The flanking PRV homology regions were from the cloned BamHI #10 fragment which contains the gpX promoter and from the cloned BamHI #7 fragment extending from the NdeI site to the BamHI site (FIG. 3). The NdeI site was filled in according to the POLYMERASE FILL-IN REACTION, and the beta-galactosidase gene was inserted between the BamHI #10 and BamHI #7 fragments. This construct positioned the beta-galactosidase gene behind the gpX promoter and the gpX poly A signal sequences with a deletion of almost all of the coding region of gpX. The plasmid DNA and DNA from wild-type PRV were mixed and transfected according to the DNA TRANSFECTION FOR GENERATING RECOMBINANT PRV procedure. The recombinant virus was screened and purified from the transfection stock by the BLUOGAL SCREEN FOR RECOMBINANT PRV procedure.

The resulting virus from this screen was designated S-PRV-014 and has been deposited with the ATCC under Accession No. VR 2135. It contained the beta-galactosidase gene in place of the gpX coding region as determined by PREPARATION OF PRV DNA followed by SOUTHERN BLOTTING OF DNA. The expression of the beta-galactosidase gene was confirmed by the BLUOGAL SCREEN FOR RECOMBINANT PRV test, and by the o-nitrophenylgalactopyranoside substrate assay (11). The structure of this virus is shown in FIG. 3D.

EXAMPLE 4

S-PRV-016

S-PRV-016 is a pseudorabies virus that has a deletion in the repeat region and a deletion in the gpX coding region. The gene for *E. coli* beta-galactosidase was inserted in place of the gpX gene and is under the control of the endogenous gpX gene promoter.

The following procedures were used to construct S-PRV-016 by homologous recombination. The flanking PRV homology regions were from the cloned BamHI #10 fragment which contains the gpX promoter and from the cloned BamHI #7 fragment extending from the NdeI site to the BamHI site (FIG. 3). The NdeI site was filled in according to the POLYMERASE FILL-IN REACTION, and the beta-galactosidase gene was inserted between the BamHI #10 and BamHI #7 fragments. This construct positioned the beta-galactosidase gene behind the gpX promoter and the gpX poly A signal sequences with a deletion of almost all of the coding region of gpX. The plasmid DNA and the DNA from S-PRV-001 (ATCC Accession No. VR 2106) were mixed and transfected according to the DNA TRANSFECTION FOR GENERATING RECOMBINANT PRV procedure. The recombinant virus was screened and purified from the transfection stock by the BLUOGAL SCREEN FOR RECOMBINANT PRV procedure.

The resulting virus from this screen was designated S-PRV-016 and has been deposited with the ATCC under Accession No. VR 2136. It contains the beta-galactosidase gene in place of the gpX coding region as determined by PREPARATION OF PRV DNA followed by SOUTHERN BLOTTING OF DNA. The expression of the beta-galactosidase gene was confirmed by the BLUOGAL SCREEN FOR RECOMBINANT PRV test and by the o-nitrophenylgalactopyranoside substrate (11). The structure of this virus is shown in FIG. 3E.

EXAMPLE 5

S-PRV-020

S-PRV-020 is a pseudorabies virus that contains a deletion in the TK gene, a deletion in the repeat regions, and a deletion of the gpX gene, with an insertion of the swine parvovirus B capsid protein gene into the gpX region.

For cloning the swine parvovirus B gene, the NADL-8 strain double-stranded replicative-form DNA was purified from swine parvovirus infected cells and was supplied by Dr. T Molitor, University of Minnesota. The parvovirus NADL-8 DNA was cloned into the *E. coli* plasmid pSP64 by methods detailed in (15). The DNA was partially sequenced to allow the determination of the start and the end of the major caspid protein gene, the B gene. Identification was confirmed by comparison of related sequences in the rat HI parvovirus capsid gene (20, 21).

The PRV glycoprotein X (gpX) gene promoter was used to express the B gene and the gpX poly A signal sequence was used to terminate transcription. The parvovirus B gene from AccI site at nucleotide #391 to the RsaI site at nucleotide #2051 was cloned between the BamHI and NdeI site of gpX (see FIG. 7A and B). Plasmid pSY864 contained this fragment of the parvovirus B gene flanked by the gpX signal sequence as shown in FIG. 7 It was used as the homologous DNA to promote homologous recombination between S-PRV-013 DNA and the plasmid DNA to facilitate the incorporation of the B gene into the PRV genome. The plasmid DNA and S-PRV-013 DNA were mixed and transfected together according to the DNA TRANSFECTION FOR GENERATING RECOMBINANT VIRUS procedure. The recombinant virus was screened and purified for the transfection stock by the BLUOGAL SCREEN FOR RECOMBINANT PRV procedure with the following modification. Because the parental S-PRV-013 contained the beta-galactosidase gene, it generated blue plaques in the screening procedure. Since the parvovirus B gene would replace the beta-galactosidase gene in the virus, the plaques with this insert would appear colorless. Therefore, colorless plaques were picked and analyzed during this screening. A virus that contained the B gene was isolated from this screening and was called S-PRV-020.

DNA from S-PRV-020 was isolated by the PREPARATION OF PRV DNA procedure and used to confirm the insertion of the parvovirus B gene according to the SOUTHERN BLOTTING OF DNA procedure using the B gene as a probe. The test showed that the parvovirus B gene had been incorporated into the PRV genome as expected. The structure of S-PRV-020 is shown in FIG. 7C. S-PRV-020 has been deposited with the ATCC under Accession No. VR 2137.

EXAMPLE 6

S-PRV-029

S-PRV-029 is a pseudorabies virus that has a deletion in the junction region between the unique long DNA and the internal repeat of PRV, and a deletion in the gpX gene in the unique short region. The *E. coli* beta-galactosidase gene under the control of the gpX promoter and polyadenylation signals has been inserted into both deletions in S-PRV-029.

To construct this virus, the SalI #1 fragment of PRV was first cloned. PRV DNA was prepared and then cut with SalI restriction enzyme. The cut DNA was electrophoresed on an agarose gel and the largest SalI band (15 kb) was purified from the gel (see PHENOL EXTRACTION OF DNA FROM AGAROSE). The purified DNA was ligated into the plasmid pSP64 (see LIGATION) and the DNA mixture was used to transform *E. coli* HB101 according to Maniatis et al. (15). The SalI #1 clone was mapped for restriction sites.

The homologous recombination procedure was used to construct S-PRV-029. The exact position of the junction region was determined by sequencing the DNA from SalI #1 fragment. It was found that the junction region was positioned between two StuI sites (see FIG. 6B). Two fragments of DNA from the SalI clone were used to create the homology vector for recombination. One was a fragment from BamHI #8′ from StuI to BamHI and the other was from BamHI to StuI (see FIG. 6B).

The *E. coli* beta-galactosidase gene was previously engineered to contain the gpX promoter and polyadenylation signals as described for S-PRV-013. To put this B-galactosidase gene into the junction region clone, a HindIII linker was first inserted into the StuI site between the BamHI #8 and BamHI #8′, and into this HindIII site was cloned a HindIII fragment containing the beta-galactosidase gene with the gpX signals.

The resulting plasmid plus wild-type PRV DNA were transfected into Vero cells by the DNA TRANSFECTION FOR GENERATING RECOMBINANT VIRUS procedure. A virus was isolated from the transfection stock that contained the beta-galactosidase gene inserted into both the junction deletion (FIG. 6B) and the gpX deletion (FIG. 6A) due to the presence of homology to both of these regions in the plasmid. This virus was purified by the BLUOGAL SCREEN FOR RECOMBINANT PRV procedure and was designated S-PRV-029.

S-PRV-029 was shown to be expressing beta-galactosidase by the BLUOGAL SCREEN FOR RECOMBINANT PRV procedure and the o-nitrophenylgalactopyranoside assay (11) and has been deposited with the ATCC under Accession No. 2139. The structure of this virus is shown in FIG. 6C.

EXAMPLE 7

The present invention involves the use of genetically engineered herpesviruses to protect animals against disease. It was not apparent at the outset of research which deletions in herpesviruses would serve to attenuate the viruses to the proper degree so as to render them useful as vaccines. Even testing vaccine candidates in animal models, i.e. mouse, does not serve as a valid indicator of the safety and efficacy of the vaccine in the target animal species, i.e. swine. To illustrate this point more clearly, Table IV shows summary data of the safety and efficacy of various pseudorabies viruses which were constructed and tested in swine according to the VACCINATION STUDIES IN SWINE procedure.

TABLE IV
SUMMARY OF STUDIES CONDUCTED IN PIGS WITH VARIOUS PSEUDORABIES VIRUS CONSTRUCTS

| Construct (Deletions/Insertions)[1] | Number of Pigs | Age of Pigs | Post-Vaccination Antibody Range | Clinical Signs | Percent Protection Against Challenge |
|---|---|---|---|---|---|
| S-PRV-001 (A) | 9 | 4-6 weeks | 1:32->1:64 | Yes (22%) | Not Done |
| S-PRV-002 (A, B) | 12 | 4-6 weeks | 1:4-1:64 | None | 100 |
| S-PRV-003 (B) | 8 | 4-6 weeks | <1:2-1:16 | None | 50 |
| S-PRV-004 (B, C) | 6 | 4-6 weeks | 1:4-1:32 | None | 64 |
| S-PRV-010 (A, B, E) | 30 | 4-6 weeks | <1:2-1:16 | Yes (13%) | 100 |
| | 30 | 3-4 days | 1:4-1:64 | Yes (13%) | 100 |
| S-PRV-013 (A, B, D, E) | 23 | 4-6 weeks | <1:2-1:8 | None | 100 |
| | 25 | 3-4 days | 1:4-1:64 | None | 100 |
| S-PRV-014 (D, E) | 5 | 4-6 weeks | 1:4-1:8 | Yes (40%) | 100 |
| S-PRV-016 (A, D, E) | 5 | 4-6 weeks | 1:4-1:8 | None | 100 |

[1]A-Repeats; B-TK; C-Junction; D-gpX; E-beta-galactosidase insert

The eight constructs that have been tested have the following deletions and insertions in the genome of the virulent Shope strain of PRV: S-PRV-001 has a deletion in both repeat regions; S-PRV-002 has a deletion in both repeat regions and in the thymidine kinase gene; S-PRV-003 has a deletion in the thymidine kinase gene; S-PRV-004 has a deletion in the thymidine kinase gene and at the junction of the long unique and internal inverted repeat region; S-PRV-010 was derived from S-PRV-002 by inserting the *E. coli* lac Z gene into the deletions in the repeat regions; S-PRV-013, S-PRV-014 and S-PRV-016 are described in Examples #2, 3 and 4.

A superior vaccine product must not produce clinical signs in 3-4 day old piglets (the more sensitive age) and give 100% protection in pigs of all ages. From Table IV, it is apparent that each vaccine candidate provided some degree of attenuation and protection in swine, but each vaccine provided a unique response. The best vaccine candidate from this list to date is S-PRV-013, which contains three deletions; one in the repeat region, one in the TK gene, and one in the gpX gene. The utility of this combination of deletions was unexpected. These results are novel, unpredicted, and useful in the selection of a superior pseudorabies vaccine product.

References

1. R. W. Price and A. Kahn, Infection and Immunity 34, 571–580, 1981.
2. P.B. Tenser, et al., Journal of General Virology 64, 1369–1373, 1983.
3. S. Kit, et al., Ninth International Herpesvirus Workshop, Seattle, Aug. 24–29, 1984.
4. Roizman, et al., Coldspring Harbor Conference on New Aproaches to Viral Vaccines, September, 1983.
5. R. L. Thompson, et al., Virology 131, 180–192, 1983.
6. K. Fukuchi, et al., Proc. Natl. Acad. Sci. (USA) 82, 751–754, 1985.
7. J. M. Koomey, et al., Journal of Virology 50, 662–665, 1984.
8. B. Lomniczi, et al., Journal of Virology 49, 970–979, 1984.
9. S. Ihara, et al., Virology 122, 268–278, 1982.
10. T. J. Rea, et al., J. of Virology 54, 21–29, 1985.
11. P A. Norton and J. M. Coffin, Molecular and Cellular Biology 5, 281–290, 1985.
12. F. L. Graham and A. Van der Eb., Virology 52 556–567, 1973.
13. T. C. Holland, et al., Journal of Virology, 52, 566–574, 1984.
14. A. E. Churchill, et al., Journal of General Virology 4, 557–563, 1969.
15. T. Maniatis, et al., Molecular Cloning: A Laboratory Manual, Cold Spring Harbor Laboratory Press, 1982.
16. L.E. Post, et al., Cell 24, 555–565, 1981.
17. J. Campione-Piccardo, et al., J. Virology 31, 281–287, 1979.
18. M.W. Wathan and L.M.K. Wathan, Journal of Virology 58, 173–178, 1986.
19. T.C. Mettenleiter, et al., Journal of Virology 56, 307–311, 1985.
20. S.R. Rhode and P.R. Paradiso, Journal of Virology 45, 173–184, 1983.
21. P.R. Paradiso, et al., Journal of Virology 52, 77–81, 1984.
22. J.T. Van Oirschot, et al., Journal of General Virology 67, 1179–1182, 1986.

What is claimed is:

1. A vaccine which comprises an effective immunizing amount of an attenuated pseudorabies virus designated S-PRV-013 (ATCC Accession No. VR 2120) and a suitable carrier.

2. A method of immunizing an animal against pseudorabies virus which comprises administering to the animal an immunizing dose of the vaccine of claim 1.

3. The method of claim 2, wherein the animal is a swine.

4. A method for distinguishing an animal vaccinated with the vaccine of claim 1 from an animal infected with a naturally-occurring pseudorabies virus which comprises analyzing a sample of a body fluid from the animal for the presence of glycoprotein X and at least one other antigen normally expressed in an animal infected by a naturally-occurring pseudorabies virus, identifying antigens which are present in the body fluid and determining whether glycoprotein X is present in the body fluid, the presence of antigens which are normally expressed in an animal by a naturally-occurring pseudorabies virus and the absence of glycoprotein X in the body fluid being indicative of an animal vaccinated with the vaccine and not infected with a naturally-occurring pseudorabies virus.

5. The method of claim 4, wherein the presence of antigens and glycoprotein X in the body fluid is determined by detecting in the body fluid antibodies specific for the antigens and glycoprotein X.

6. A method for distinguishing an animal vaccinated with the vaccine of claim 1 from an animal infected with a naturally-occurring pseudorabies virus which comprises analyzing a sample of a body fluid from the animal for the presence of glycoprotein X and at least one other antigen expressed in an animal vaccinated with S-PRV-013, identifying antigens which are present in the body fluid and determining whether glycoprotein X is present in the body fluid, the presence of an antigen which is expressed in an animal vaccinated with S-PRV-013 and the absence of glycoprotein X in the body fluid being indicative of an animal vaccinated with the vaccine and not infected with a naturally-occurring pseudorabies virus.

7. A method of claim 6 wherein the antigen expressed in an animal vaccinated with S-PRV-013 is $\beta$-galactosidase.

* * * * *